United States Patent [19]

Nielsen

[11] Patent Number: 4,872,235

[45] Date of Patent: Oct. 10, 1989

[54] APPARATUS FOR CLEANING MEDICAL HAND INSTRUMENTS AND IMPLEMENTS FOR TREATMENT OF THE HAIR, SKIN AND/OR BODY

[76] Inventor: Ernst P. F. Nielsen, Berliner Str. 24, D-6090, Ruesselsheim, Fed. Rep. of Germany

[21] Appl. No.: 152,106

[22] Filed: Feb. 4, 1988

[30] Foreign Application Priority Data

Feb. 12, 1987 [DE] Fed. Rep. of Germany ....... 8702105
Apr. 25, 1987 [DE] Fed. Rep. of Germany ....... 8706008

[51] Int. Cl.$^4$ ............................................. A46B 17/06
[52] U.S. Cl. ................................................. 15/104.92
[58] Field of Search ...................... 15/104.92, 400, 76, 15/104.9

[56] References Cited

U.S. PATENT DOCUMENTS

| | | | |
|---|---|---|---|
| 2,839,769 | 6/1958 | Vacanti | 15/76 X |
| 3,413,672 | 12/1968 | Gallo | 15/76 |
| 3,428,988 | 2/1969 | Blackburn | 15/104.92 X |
| 3,745,605 | 7/1973 | Gitschel et al. | 15/400 |
| 4,087,878 | 9/1978 | Grieshaber et al. | 15/104.92 X |
| 4,380,839 | 4/1983 | Coradonna | 15/104.92 |

FOREIGN PATENT DOCUMENTS 1040414 5/1953 France ............................... 15/104.92

Primary Examiner—Chris K. Moore
Attorney, Agent, or Firm—Barnes, Kisselle, Raisch, Choate, Whitemore & Hulbert

[57] ABSTRACT

In view of increased risks for physicians and personnel to catch old and new virus infections like hepatitis-B and aids, the invention provides pre-cleaning of medical hand instruments by mechanical cleaning means, e.g. brushes (38, 39) lamellas or plastic pads disposed below the liquid surface of a disinfecting solution in a possibly closed cleaning container (31) or in a cleaning trough (30).

Proposed are advantageous embodiments preventing a spattering of contaminated particles into the environment. In this connection it is proposed to use an additional disinfecting trough (41) at the work place serving as an emergency relief aid for persons injured at the work place. The invention may be used also in non-medical practices, e.g. in barber, manicure, pedicure, cosmetic and tatooing shops and offices to protect the personnel and clients from infections.

17 Claims, 1 Drawing Sheet

APPARATUS FOR CLEANING MEDICAL HAND INSTRUMENTS AND IMPLEMENTS FOR TREATMENT OF THE HAIR, SKIN AND/OR BODY

The invention relates in particular to an apparatus for cleaning medical hand instruments for medical practices, medical and biological laboratories as well as surgery rooms.

After use of medical hand instruments it is usual to pre-clean them prior to a final sterilization thereof in an autoclave. This is performed generally such that the instruments collected during a certain time period are cleansed with flowing water above a wash basin by means of mechanical cleaning means, e.g. brushes or the like. This cleaning mechanically removes tissue particles adhering to the instruments and quite often conglutinated or crusted blood, saliva, etc. Thereafter the instruments are immersed in a disinfecting solution for further treatment.

During the above-described coarse cleaning of the instruments the personnel and the physicians undergo an increased infection risk. The mechanical removal and brushing, respectively—even if carefully performed—bears not the risk that particles of the contaminated substances adhering to the instruments are spattered and may enter the blood path of the handling persons even if only slightly injured.

In dental practices, e.g., it may happen that the dentist injures his hands during treatment of a patient. Wearing rubber gloves does not provide for a sufficient protection since the thin material of the gloves may be perforated with the injury so that there is a risk of a direct infiltration of infecting substances.

Nowadays these risks are particularly high in view of expanding old and new virus infections like hepatitis-B and AIDS.

According to the invention the apparatus may further serve to clean hand implements for treatment of the hair, skin and/or body, as used e.g. in barber, pedicure, manicure and cosmetical shops and offices. These hand implements generally comprise brushes, scissors, combs, pinzers, knives, etc., as well as special devices for tatooing of the skin. Furthermore, medical hand instruments are being increasingly used by the above-mentioned shops and offices.

Even if these hand implements are carefully handled, injuries of the clients, e.g. injuries of the skin during hair cutting, shaving, removal of black-heads, fingernail cutting, etc., cannot be excluded. Generally combs, scissors and knives in barber shops do not undergo a specific mechanical disinfecting cleaning. Quite often the hand implements are only cleansed or wiped off by disinfecting cloths to remove conglutinated contaminated substances like scab, scurf, crust, blood, puss, etc. In all these cases an infection of the clients and personnel by use of the hand implements cannot be excluded.

The problem to be solved by the present invention is to avoid the above risks in a convenient manner.

According to the present invention this problem is solved by disposing mechanical cleaning means, e.g. brushes, lamellas or foam pads used for cleaning, below the liquid surface within a receptacle. This avoids an inadvertent spattering of contaminated substances, e.g. in the face, the hands, the adjacent work area or even into the ambient air. The cleaning means are one-way articles. This is why they will be fixed, e.g. by plug connectors, within the receptacle so that they may be easily and readily replaced.

Furthermore, it is proposed that the receptacle be provided with a cover having an elongated slot allowing to introduce the medical hand instrument into the receptacle for engagement with the cleaning means. This largely prevents a spattering of contaminated substances additional to the main feature of the present invention.

At least the cover should be made from transparent material, e.g. glass. This allows the user to observe movements of the instruments and to check the progress of the pre-cleaning.

To obtain a thorough cleaning of the instruments there are two cleaning means are disposed horizontally and in a mirror-symmetrical relationship relative to each other so that they contact each other. To further enhance the cleaning a third cleaning means may be provided on the bottom of the receptacle.

According to a further feature of the invention the cleaning means may be mounted to the walls of the container or to portions of the cover. In the latter case the cover is formed as a downwardly opening receptacle thereby to prevent a splashing of liquid when the instruments are rapidly moved back and forth during the cleaning.

A simplified embodiment of the present invention provides to mount one or a plurality of cleaning means in a sieve insert of a known-per-se disinfecting trough by means of suitable plug connectors. In this case the holes inherent in the sieve insert may be used to mount the cleaning means.

In order to definitely exclude infections it is furthermore proposed, according to the present invention, to use a smaller trough in combination with an above-mentioned disinfecting trough in case of an injury at the work place, which smaller trough includes a pad soaked with a special virus and germ killing solution. This allows the treating person to immediately inhibit the blood infiltration of virus and germs when the hands were injured.

In the following the invention will be further described with respect to embodiments thereof.

Figure 1:
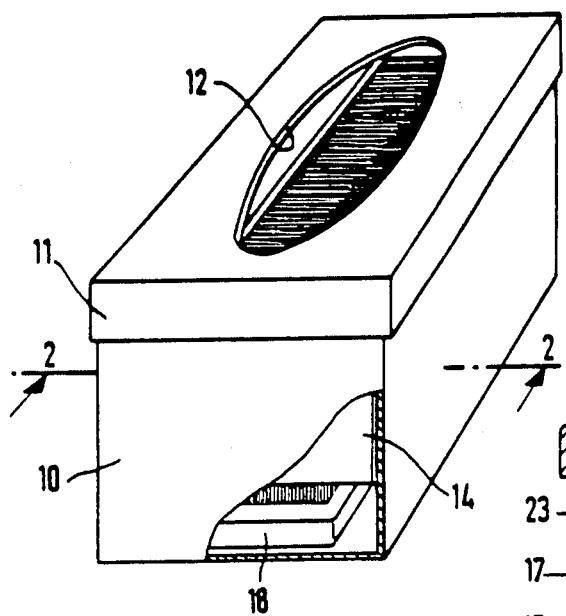
FIG. 1 shows a first embodiment of the apparatus in a perspective view.
Figure 2:
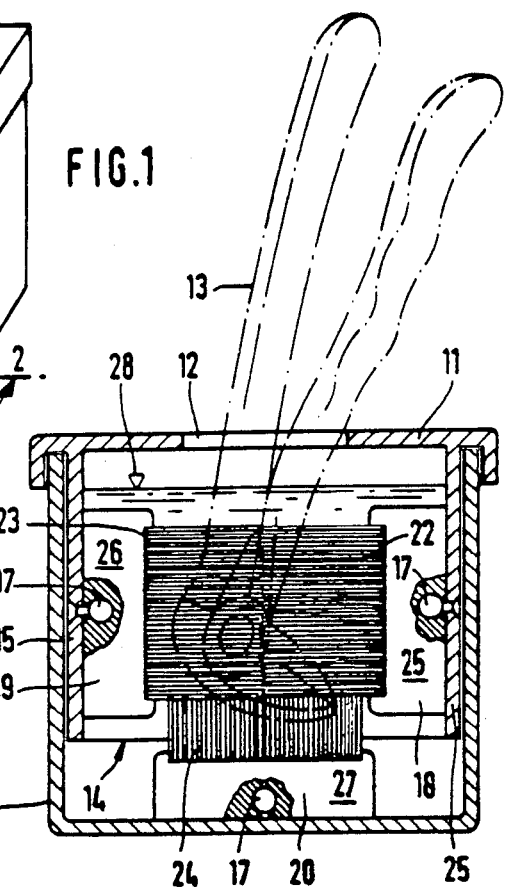
FIG. 2 is a section along lines 2—2 in FIG. 1.

The apparatus shown in FIGS. 1 and 2 comprises a container 10 and a cover 11 thereon. The container 10 has a rectangular bottom and adjacent side walls. The dimensions of the container 10 may be e.g. $30 \times 15 \times 15$ cm (length/width/height). The container 10 and cover 11 are preferably made from transparent material, preferably glass. Cover 11 has an elongated oval slot 12 allowing to introduce the mechanical hand instruments as indicated by reference numeral 13 in FIG. 2. Cover 11 is formed as a downwardly opening receptacle 14 having walls 15. The external sides of walls 15, on all sides, extend as close as possible to the internal surfaces of the container 10 to avoid spattering of liquid. The cleaning means are mounted to the internal walls of the downwardly opening receptacle 14 by known plug connectors 17.

In the embodiments of FIGS. 1 and 2 there are provided three brushes, 18, 19, 20, of which two brushes 18 and 19 are disposed horizontally and in mirror-symmetrical relationship, and a third brush 20 is mounted on the bottom of container 10 such that its bristles face upwardly. Brushes 18, 19, 20 are preferably of the same size. Their bristles 22, 23, 24 are molded into their bases 25, 26, 27. The brushes are disposed so that their bristles contact each other. All portions of the brushes are made from acid-resistent material of known composition. Reference numeral 28 refers to the liquid surface of a known disinfecting solution.

Figure 3:
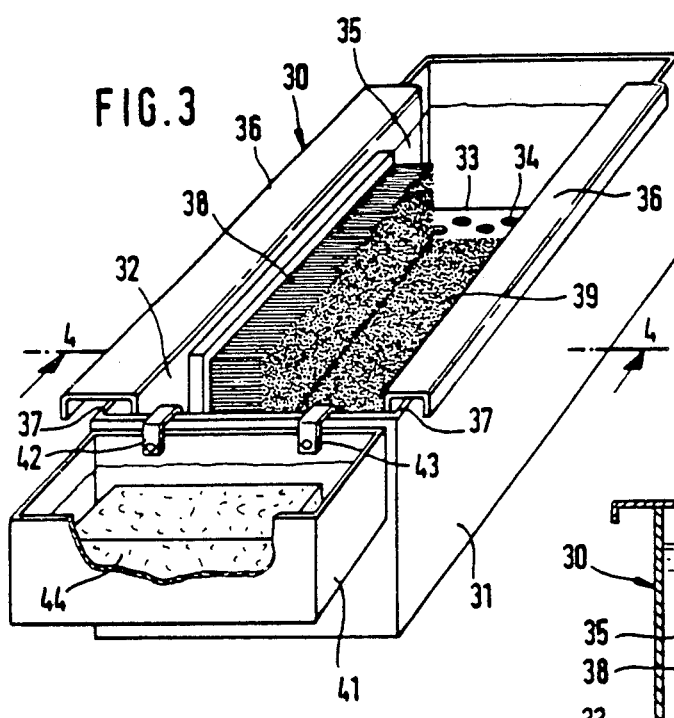
FIG. 3 shows a second embodiment of the apparatus in a perspective view.
Figure 4:
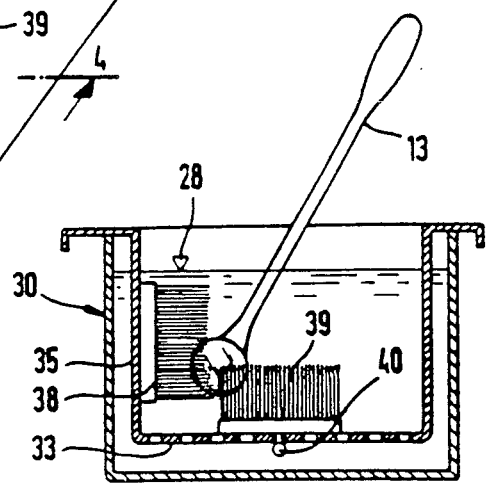
FIG. 4 is a section along lines 4—4 in FIG. 3.

The embodiment of FIGS. 3 and 4 is based on a known disinfecting trough 30. It comprises a container 31 having similar dimensions as container 10 in FIG. 1 and including a sieve insert 32. Perforated sheet 33 of sieve insert 32 including a great number of holes 34 is upwardly bent at its longitudinal sides to form a pair of legs 35. Legs 35 are provided at their upper ends with flange portions 36 resting on the edges 37 of disinfecting trough 30. The cleaning means are disposed on the sieve sheet 33 and/or legs 35. In this embodiment brushes 38, 39 are mounted to only one leg 35 and the sieve sheet 33 by plug connection 40. Of course brushes may be provided at both legs 35.

Disinfecting trough 30 is removable combined with a smaller trough 41 to be used as an immediate relief aid for injuries occurring at the work place. To this end a pair of hooks 42, 43 engage edge 37 of the disinfecting trough. The smaller trough 41 includes a plastic pad 44 soaked with a special virus and germ killing solution. This allows the treating persons to immediately disinfect any wounds (e.g. of their hands) resulting from an injury. The close neighborhood of disinfecting trough and smaller trough 41 and their positioning adjacent to the working place of the user is of particular importance.

Of course smaller trough 41 may also be combined with container 10 of the apparatus shown in FIG. 1; it may be even integral therewith if desired.

The apparatus shown in the drawing are designed in particular for medical applications, however, may be readily changed to be used also in non-medical areas. Such changes relate e.g. to the dimensions, arrangement and type of cleaning means.

I claim:

1. An apparatus for cleaning medical hand instruments and implements for treating hair, skin and/or body comprising:
    (a) a container having opposed parallel side wall means and bottom wall means orthogonal to said side wall means;
    (b) a plurality of cleaning means including at least a first cleaning means detachably affixed to said bottom wall means and a second cleaning means detachably affixed to and extending along one of said side wall means adjacent and parallel to said first cleaning means such that cleaning surface portions of said first and second cleaning means contact each other and at least partially overlap; and
    (c) a solution in said container totally immersing said cleaning means.

2. The apparatus set forth in claim 12 wherein said side wall means comprises outer side walls of said container, an open edge of said container, and an insert having inner side walls and flanges that overlie and rest upon said edge with said inner side walls positioned adjacent to said outer side walls of said container.

3. The apparatus as set forth in claim 2 wherein said first and second cleaning means comprise brushes having bristles, said first brush having upwardly extending bristles contacting and partially overlapping horizontally disposed bristles or said second brush.

4. The apparatus as set forth in claim 3 wherein said bottom wall means comprises a bottom wall bridging said outer walls and a perforated sheet adjacent said bottom wall.

5. The apparatus as set forth in claim 4 wherein said insert includes said perforated sheet integrally bridging said inner side walls, said perforated sheet and said inner side walls being adjacent to said outer side walls and said bottom wall of said container.

6. The apparatus as set forth in claim 5 further comprising a trough having a pair of hooks to releasably engage an edge of said container.

7. The apparatus as set forth in claim 6 wherein said trough has an impermeable internal surface for a disinfectant solution and a pad immersed in said solution.

8. The apparatus as set forth in claim 2 further comprising a plurality of plug connectors to detachably mount said cleaning means to said inner side walls and to said bottom wall means.

9. The apparatus as set forth in claim 2 further comprising a third cleaning means detachably affixed to a said inner side wall opposite said second cleaning means.

10. The apparatus as set forth in claim 9 wherein said first, second and third cleaning means comprise brushes having bristles, bristles of said second and third brushes being disposed horizontally in mirror symmetrical relationship and in contact with each other, said bristles of said second and third brushes partially overlapping and being in contact with upwardly extending orthogonal bristles of said first brush.

11. The apparatus as set forth in claim 10 wherein said insert comprises a removable cover for said container, said cover having an underside and said inner side walls integrally depending from said underside thereof, and having an oval slot for access to said container.

12. The apparatus as set forth in claim 11 wherein said cover is of a transparent material construction.

13. The apparatus as set forth in claim 12 wherein said first, second and third brushes are of the same size.

14. The apparatus as set forth in claim 2 wherein said solution is a liquid disinfectant.

15. The apparatus as set forth in claim 2 wherein said cleaning means are of acid resistant construction.

16. An apparatus for cleaning medical hand instruments and implements for treatment of hair, skin and/or body comprising:
    (a) a container having opposed parallel outer side walls and a bottom wall orthogonal to and bridging said outer side walls;
    (b) a cover having a slot and a downwardly extending integral insert having inner side walls positioned internally adjacent said outer side walls of said container;
    (c) a plurality of brushes having bristles, including a first brush detachably affixed to said bottom wall of said container and second and third brushes detachably affixed on opposite side walls of said insert and disposed horizontally in opposed mirror symmetrical relationship, with bristles of said second and third brushes being in contact with each other and partially overlapping and in contact with upwardly extending orthogonal bristles of said first brush;

(d) a plurality of plug connectors detachably mounting said brushes to said inner side walls of said insert and to said bottom of said container; and (e) a disinfectant solution in said container totally immersing said brushes.

17. An apparatus for cleaning medical hand instruments and implements for treatment of hair, skin and/or body comprising:
   (a) a container having open edges, opposed parallel outer side walls and a bottom wall orthogonal to and bridging said said outer walls;
   (b) an insert having inner side walls, a perforated sheet integrally bridging said inner side walls, said inner side walls being internally juxtaposed to said outer side walls of said container and having flange portions resting on said edges of said container;
   (c) a plurality of brushes having bristles including at least a first brush detachably affixed to and extending along one inner side wall of said insert and a second brush detachably affixed to said perforated sheet parallel to said first brush such that bristles of said first and second brushes contact each other and partially overlap;
   (d) a plurality of plug connectors detachably mounting said brushes to said inner side wall and said perforated sheet;
   (e) a disinfectant solution in said container totally immersing all said brushes; and
   (f) a trough having a disinfectant solution, a pad immersed in said solution and a pair of hooks removably engaging said edge of said container.

* * * * *